United States Patent [19]

Bottelberghe

[11] Patent Number: 4,908,463
[45] Date of Patent: Mar. 13, 1990

[54] ALUMINOXANE PROCESS

[75] Inventor: Scott A. Bottelberghe, Port Allen, La.

[73] Assignee: Ethyl Corporation, Richmond, Va.

[21] Appl. No.: 279,496

[22] Filed: Dec. 5, 1988

[51] Int. Cl.[4] .............................................. C07F 5/06
[52] U.S. Cl. .................................................... 556/179
[58] Field of Search ......................................... 556/179

[56] References Cited

U.S. PATENT DOCUMENTS 3,300,458  1/1967  Manyik et al. .................. 526/169
4,730,071  3/1988  Schoenthal et al. .
4,730,072  3/1988  Schoenthal et al. .
4,772,736  9/1988  Edwards et al. .

FOREIGN PATENT DOCUMENTS 102562  6/1976  Poland .

Primary Examiner—Paul F. Shaver
Attorney, Agent, or Firm—Joseph D. Odenweller

[57] ABSTRACT

Hydrocarbylaluminoxanes, especially methylaluminoxane, having high catalytic activity in the polymerization of olefins are made in high yield and low gel content by impinging (1) a solution of a hydrocarbyl aluminum, e.g. trimethyl aluminum, in an inert solvent, e.g. toluene, with (2) a water dispersion in an inert solvent (e.g. toluene) in a T-shaped reactor such that the hydrocarbyl aluminum and water immediately react to form an aluminoxane solution which is promptly removed from the T-shaped reactor through its third arm. The water dispersion is formed by passing a solvent/water mixture through a static mixer which comprises a plurality of deflection vanes forming a tortuous path through the static mixer causing extremely turbulent flow.

19 Claims, 2 Drawing Sheets

ALUMINOXANE PROCESS

BACKGROUND

Vandenberg, U.S. Pat. No. 3,219,591, reported the catalytic activity of compounds formed by the reaction of trialkyl aluminum with limited amounts of water in the polymerization of epichlorohydrin and other oxiranes. Shortly thereafter Manyik et al., U.S. Pat. No. 3,242,099, reported the use of aluminoxanes, made by reacting 0.85-1.05 moles of water with hydrocarbyl aluminum compounds such as triisobutyl aluminum, as co-catalysts with certain transition metal compounds in the polymerization of mono-unsaturate α-olefins; e.g. ethylene, propylene. Isobutylaluminoxane was made by adding an equal mole quantity of water to a heptane solution of triisobutyl aluminum.

Manyik et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Sinn et al. U.S. Pat. No. 4,404,344 prepare methylaluminoxane by adding trimethyl aluminum to a slurry of $CuSO_4 \cdot 5H_2O$ in toluene. Water as a metal hydrate controls its reactivity with the trimethyl aluminum. Kaminsky et al. U.S. Pat. No. 4,544,762 is similar except it uses an aluminum salt hydrate to supply the water. Likewise Welborn et al. U.S. Pat. No. 4,665,208 describe the use of other metal salt hydrates such as $FeSO_4 \cdot 7H_2O$ as a water source in preparing aluminoxane.

Schoenthal et al. U.S. Pat. No. 4,730,071 show the preparation of methylaluminoxane by dispersing water in toluene using an ultrasonic bath to cause the dispersion and then adding a toluene solution of trimethyl aluminum to the dispersion. Schoenthal et al. U.S. Pat. No. 4,730,072 is similar except it uses a high speed, high shear-inducing impeller to form the water dispersion.

Edwards et al. U.S. Pat. No. 4,772,736 describe an aluminoxane process in which water is introduced below the surface of a solution of hydrocarbyl aluminum adjacent to a stirrer which serves to immediately disperse the water in the hydrocarbon solution.

SUMMARY

The present process uses a static mixer to disperse water in an inert solvent and then impinges the water dispersion with a solution of a hydrocarbyl aluminum compound in a substantially T-shaped reactor. The confluent reaction mixture is promptly removed from the T-shaped reactor to a finishing reaction vessel where the reaction is completed in the absence of excess water.

DESCRIPTION OF THE DRAWING

FIG. I is a schematic flow diagram of the process showing confluence of the hydrocarbyl aluminum solution with the water dispersion in the T-shaped reactor to form a single outlet stream.

FIG. II is another flow diagram showing the T-reactor located inside the finishing reaction vessel.

DESCRIPTION OF THE PREFERRED EMBODIMENT

Figure 1:
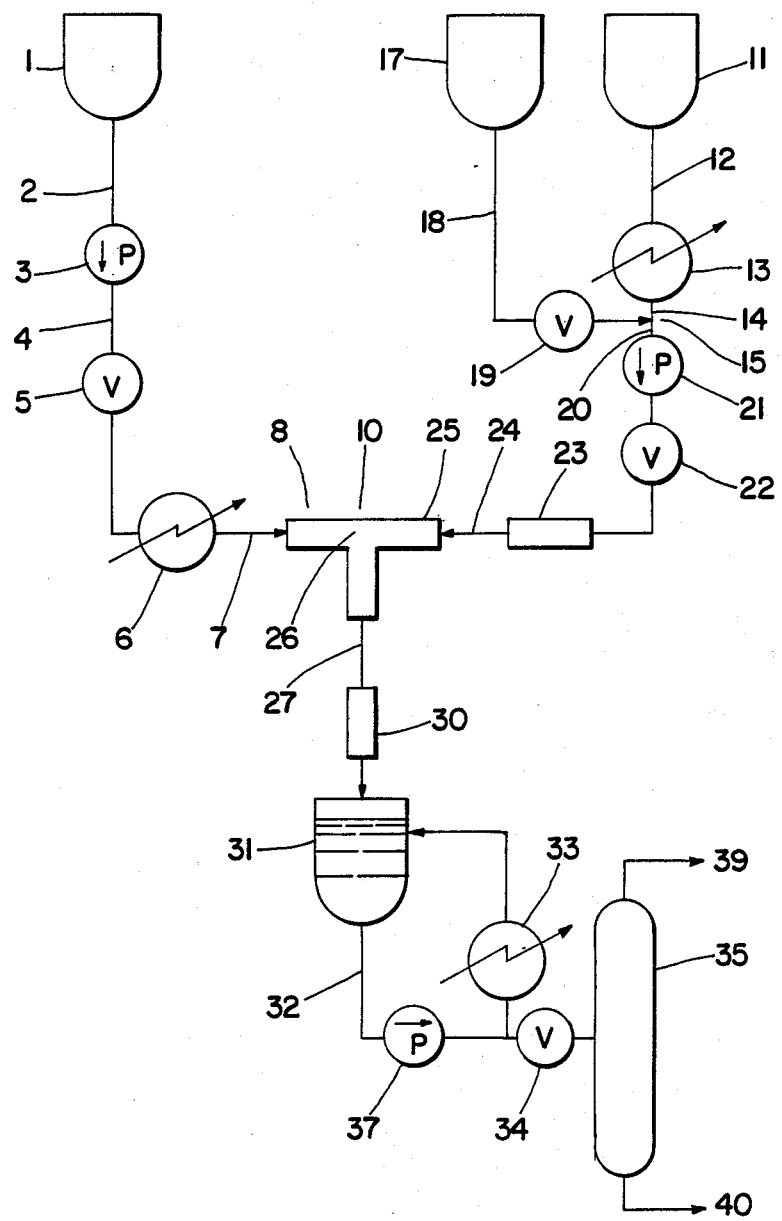
Figure 2:
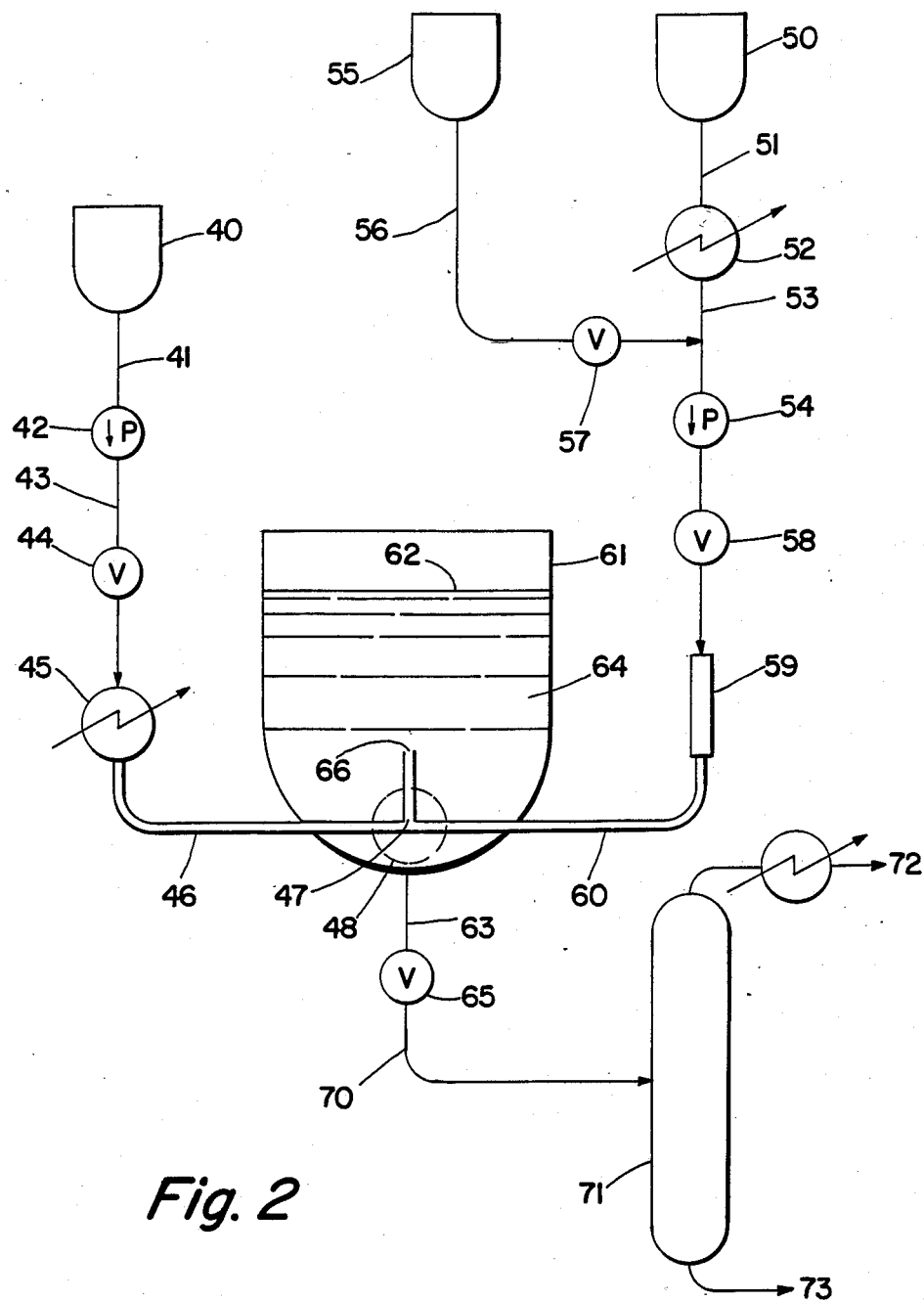

A preferred embodiment of the invention is a process for making a hydrocarbyl aluminoxane, said process comprising:
(A) forming a solution of a hydrocarbyl aluminum compound in a dry inert hydrocarbon solvent,
(B) conducting an inert hydrocarbon solvent containing a separate water phase through a static mixer comprising a plurality of deflection elements which provide a tortuous path through said static mixer thereby dispersing said water in the hydrocarbon solvent to form a water dispersion,
(C) conducting both (1) said hydrocarbyl aluminum compound solution and (2) said water dispersion to a reaction zone whereby said hydrocarbyl aluminum compound solution and said water dispersion enter said reaction zone and co-mingle, one with the other, and react to form a hydrocarbyl aluminoxane solution further characterized in that the ratio of aluminum atoms to moles of water entering said reaction zone is in the range of 1:1 to 2:1, and
(D) promptly removing said hydrocarbyl aluminoxane solution from said reaction zone.

Any aluminum compound capable of reacting with water to form an aluminoxane can be used. This includes trialkyl aluminum, triaryl aluminum, mixed alkyl aryl aluminum, alkyl aluminum dihalides, dialkyl aluminum halides, alkylaluminum sesquihalides, dialkyl aluminum alkoxides and the like.

The preferred aluminum compounds are the hydrocarbyl aluminum compounds, especially trialkyl aluminum compounds such as trimethyl aluminum, triethyl aluminum, triisobutyl aluminum, tri-n-hexyl aluminum, tri-octyl aluminum and the like. Of these the more preferred are the tri-$C_{1-4}$-alkylaluminum compounds.

Of the various hydrocarbyl aluminoxanes, the more difficult to prepare are methylaluminoxane and ethylaluminoxane because of the extreme reactivity of trimethyl aluminum and triethyl aluminum with water. The most reactive is trimethyl aluminum and accordingly the most preferred embodiment is the application of the process to make methylaluminoxane.

Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The concentration of the hydrocarbyl aluminum compound in the inert solvent can range from about 1-30 weight percent. A preferred concentration is about 5-20 weight percent, more preferably 10-15 weight percent. The hydrocarbyl aluminum solution is conducted to one inlet of the T-reactor.

The second feed stream to the T-reactor is a water dispersion. The water dispersion can be in any inert hydrocarbon solvent such as those previously listed as hydrocarbyl aluminum solvents. Preferably the same solvent is used.

Water can be added to the inert solvent by any method. In a preferred method the water is added by means of in-line blending upstream from the static mixer. The amount of water added is about 0.25-5.0 weight percent based on the weight of inert hydrocarbon solvent. A more preferred amount of water is about 0.5-3.0 weight percent and most preferably about 1.0-2.5 weight percent.

The water/inert solvent mixture is pumped through a static mixer at a high rate to form a water dispersion. A static mixer is a unit used in the chemical industry to mix two or more components, at least one of which is liquid. It is usually in the form of a conduit containing a plurality of fixed vanes or deflection elements which force the feed to take a tortuous path through the mixer creating a high degree of turbulence. Suitable static mixers are available from chemical equipment companies such as Koch Engineering Company, Inc., Houston, Tex.

After passing through the static mixer the resultant water dispersion is conducted to the second inlet of the T-reactor wherein it co-mingles with the hydrocarbyl aluminum solution at the point of confluence. The ratio of the hydrocarbyl aluminum stream and the water dispersion is such that the ratio of aluminum atoms to moles of water entering the T-reactor is about 1:1 to 2:1.

Although not essential, both the hydrocarbyl aluminum solution and the water dispersion are preferably cooled prior to introduction into the T-reactor. The cool inert solvent provides a heat sink for heat released in the T-reactor. The feed streams are preferably cooled below 20° C. to as low as −70° C. or even lower depending on the freezing point of the solution. The water dispersion will form ice crystals at the very low temperatures. A preferred temperature range is about 20° C. to −20° C. In a more preferred embodiment the hydrocarbyl aluminum solution is cooled to 10° to −20° C. and the water dispersion is cooled to 0° to 10° C.

The reactor is referred to as a T-reactor. It need not be in the configuration of a perfect T but can have its arms raised as in a Y or its arms drooped as in . Likewise the T-reactor need not be oriented as an upright T or Y but can be inverted. The important feature is that the two feed streams converge in the reactor to co-mingle and form a confluent stream which is promptly removed from the point of confluence. This is important because the initial reaction of the hydrocarbyl aluminum and water forms a hydrocarbylaluminoxane. The aluminoxane is still very reactive with water and if it contacts more water it will continue to react to form alumina gel. In a tank type reactor in which the stoichiometric amount of water and hydrocarbyl aluminum are mixed, the hydrocarbylaluminoxane that initially forms can compete with the still unreacted hydrocarbyl aluminum for the water. This tends to form an excessive amount of insoluble gel and leaves a substantial amount of the hydrocarbyl aluminum unreacted.

In the present reactor design the initially formed mixture is almost immediately removed from the point of confluence and moves in a plug-flow manner out the exit of the T-reactor. It is not really meaningful to refer to the residence time in the T-reactor because the entire outlet conduit leading to the finishing reactor can be considered as part of the reaction zone. Residence time in the outlet conduit is not critical because the outlet solution will not contact the additional water entering the T-reactor at the point of confluence. As a practical matter residence time in the outlet conduit downstream from the point of confluence can range from about 1 milisecond to 1 minute depending upon feed rate of the two inlet streams and the diameter and length of the outlet conduit. Preferably the feed rates and outlet conduit diameter are such that the fluid velocity through the outlet conduit is fairly high—on the order of 0.5–10 ft/sec. Likewise the feed rate of each input stream and the diameter of each inlet conduit are such that the two streams are moving at 0.5–20 ft/second when they impinge, more preferably about 5–15 ft/sec.

In a further embodiment, a second static mixer is placed in the outlet conduit between the T-reactor and the finishing reaction vessel. This serves to increase turbulent flow and provide intimate contact of the components in the outlet stream. However, this static mixer need not be present.

The outlet hydrocarbyl aluminoxane solution is usually held for a short time in what is referred to as a finishing reactor. This is a tank-type reactor and is usually provided with some form of mixing such as a paddle stirrer or an external pump-around loop. The finishing reactor can also be provided with cooling means such as a coolant jacket or a heat-exchanger in an external loop.

Product solution withdrawn from the finishing reactor usually contains excess solvent and some unreacted hydrocarbyl aluminum. Solvent and unreacted hydrocarbyl aluminum can be distilled out. For example toluene boils at 107° C. and trimethyl aluminum boils at 127° C. so will tend to co-distill in a simple flash distillation. The distillation can be conducted at atmospheric or under vacuum. The final product is preferably in the form of a 5–20 weight percent solution of the hydrocarbyl aluminoxane in the inert solvent. The distillation can, however, be continued to yield a dry powder aluminoxane but this is more difficult to handle.

Referring now to FIG. I, an embodiment of the process will be described in more detail.

The process equipment includes a storage tank 1 for a 12 weight percent solution of trimethyl aluminum (TMA) in toluene connected by conduit 2 to pump 3. Pump 3 delivers the TMA/toluene solution through conduit 4 and control valve 5 to refrigerated heat exchanger 6 which cools the TMA solution to about −10° C. It is then conveyed through conduit 7 to the first arm 8 of T-reactor 10.

Storage tank 11 contains toluene and is connected by conduit 12 to heat exchanger (cooler) 13 which cools the toluene to about 5° C. The cooled toluene then passes through conduit 14 to in-line water blender 15.

Deionized water tank 17 connects through conduit 18 and control valve 19 to in-line blender 15 which functions to introduce about 1.8 weight percent water into the toluene (1.8% water/98.2% toluene). This mixture is conducted through conduit 20 to pump 21 and then through control valve 22 to static mixer 23. Although several commercial static mixers are suitable, good results have been achieved using a Koch SMV static mixer (Koch Engineering Co., Inc.). In passing through the static mixer the toluene/water mixture forms a water dispersion which is conducted at high speed (approximately >2 ft/sec) through conduit 24 to a second arm 25 of T-reactor 10. The water dispersion and the TMA/toluene solution impinge in T-reactor 10 at the point of confluence 26 and immediately co-mingle and react to form methylaluminoxane (MAO). Since the volume at the point of confluence is small the MAO solution is quickly discharged through outlet conduit 27.

It then passes through static mixer 30 into finishing reaction vessel 31. Cooling is provided for vessel 31 by heat exchanger 33 in an external pump-around loop but could also be provided by jacketing vessel 31. MAO/toluene solution is removed through control valve 34 at a rate that maintains a substantially constant liquid level in vessel 31. MAO/toluene solution passes to flash vaporizer 35 which serves to remove TMA and toluene vapor containing about 1 weight percent TMA overhead 39. The vapors are condensed and the condensate can be used in making toluene/TMA solution for storage tank 1. Product is about 10.7 weight percent MAO solution and is removed as a bottoms stream 40.

Occasionally pluggage has occurred in the outlet conduit from the T-reactor. FIG. II shows an embodiment of the invention that serves to alleviate this occasional problem. In this embodiment the T-reactor is located inside the finishing reactor below the liquid surface such that it is contacted by the aluminoxane solution in the finishing reactor and discharges its confluent liquid stream beneath the liquid surface.

Referring to Figure II, storage tank 40 containing an inert hydrocarbon solution of TMA is conveyed by conduit 41 to pump 42. Pump 42 delivers the TMA solution through conduit 43 and control valve 44 to cooler 45. The TMA solution is then conveyed at high velocity (e.g. 0.5–20 ft/sec, preferably 5–15 ft/sec) through conduit 46 to point of confluence 47 of T-reactor 48.

Storage tank 50 holds inert liquid hydrocarbon solvent (e.g. toluene) and is conected by conduit 51 to cooler 52 and then via conduit 53 to pump 54.

Tank 55 holds deionized water and is connected by conduit 56 through control valve 57 and then merges with conduit 53 for in-line blending of water at a controlled rate into the inert hydrocarbon solvent. The solvent/water blend is forced by pump 54 through control valve 58 into static mixer 59. The solvent/water blend forms a water dispersion in passing through static mixer 59 and is conveyed at high velocity through conduit 60 to the point of confluence 47 of T-reactor 48.

T-reactor 48 (shown circumscribed by a dashed line) is located inside finishing reaction vessel 61 beneath the liquid level 62. Conduit 63 removes aluminoxane solution 64 from vessel 61 through control valve 65 at a rate that maintains a substantially constant liquid level 62. Outlet 66 of T-reactor 48 discharges aluminoxane solution directly into the liquid phase in vessel 61.

Aluminoxane solution is conveyed through conduit 70 to flash vaporizer 71. Inert solvent and TMA vapor is removed overhead and condensed to form a TMA solution 72 which can be used in preparing the TMA/inert hydrocarbon solution charged to storage tank 40. Product MAO solution is removed as a bottoms product 73.

Before proceeding with a description of specific examples, the test used to evaluate the product will be described. MAO products made by various processes result in polymerization catalysts of different activity even though chemical analysis of the various products is very similar. This appears to be because of the different polymeric structures and molecular weights possible with MAO. Since the prime use of aluminoxanes is as a co-catalyst with a transitional metal compound in the polymerization of olefins, a measure of this property is the most important attribute of the aluminoxane.

The activity test used by applicants involves the preparation of a catalyst complex and the use of this complex in an actual polymerization. The test procedure is similar to the process described in Ishihara et al., U.S. Pat. No. 4,680,353, incorporated herein by reference. It involves the use of a titanium compound, e.g. titanium tetraethoxide, and an alkylaluminoxane, e.g. MAO, in the polymerization of styrene to form syndiotactic polystyrene.

Syndiotactic Polymerization Catalyst Activity Test

The tests are conducted by placing about 16 m moles (assume 58 g/mole) of MAO in a vial and adding about 96 m moles of styrene monomer. The styrene/MAO solution is held at 50° C. and 0.16 mL of a 0.1 molar solution of titanium tetraethoxide in toluene is added. After holding 2 hours at 50° C. the mixture is quenched with several mL of methanol. The insoluble polymer is removed, washed with methanol and dried. The "activity" is the percent of the styrene monomer converted to insoluble polymer. The industry accepted catalyst activity based on this test is 10–15 percent.

Another test conducted to characterize the product is the gas/Al ratio. This is conducted by first analyzing the aluminoxane solution for Al and then hydrolyzing a weighed quantity of the aluminoxane to convert the alkyl groups to a gas. Methyl groups form methane, for example. The gas volume is converted to volume at standard temperature and pressure and divided by 22.4 to obtain the moles of gas. The "moles" of Al in the same quantity of aluminoxane solution is calculated and the mole ratio of gas (e.g. methane) to Al reported. These values are usually in the range of 1.3–1.7. They do not accurately reflect the catalytic activity of the aluminoxane but do show the degree of hydrolysis achieved in the reaction forming the aluminoxane.

EXAMPLE 1

A 10 weight percent solution of trimethylaluminum (TMA) in dry toluene was prepared and placed in a storage vessel under nitrogen.

In a conduit, 1 weight percent water was blended with xylene at 5° C. and the blend pumped at 400 mL/min through an in-line static mixer (Koch SMV Static Mixer) and then through a 4.5 mm I.D. tube to one inlet of a T-reactor. The 3 arms of the T-reactor each had an I.D. of 4.5 mm.

The TMA solution was pumped through a jacketed conduit to lower its temperature to −10° C. and then through a 4.5 mm I.D. conduit at 350 mL/min to the second arm of the T-reactor.

The TMA/toluene solution and the xylene/water dispersion impinged at the intersection zone of the T-reactor. The mixture then passed almost immediately down through the third arm of the T-reactor through a 4.5 mm conduit to finishing reactor. The reaction proceeded smoothly. A total of 1822 g of MAO solution was collected in two flasks. One flask (960 g) was distilled down to 504 g. The second flask (862 g) was stripped down to 513 g.

The following table gives the results of the distillation.

|  | Before Strip | After Strip |
|---|---|---|
| Flask 1 | | |
| Net wt (g) | 960 | 504 |
| Wt % Al | 1.33 | 2.06 |
| Gas/Al ratio | 2.03 | 1.76 |
| Activity | | 25.7 |
| Flask 2 | | |
| Net wt (g) | 862 | 513 |
| Wt % Al | 1.30 | 1.63 |
| Gas/Al ratio | 2.1 | 1.95 |
| Activity | | 18.3 |

The weight percent aluminum increased after strip due to solvent removal but the actual aluminum content decreased due to the large decrease in net weight. For example, in flask 1 calculated aluminum content before strip was 12.77 g and after strip was 10.38 g indicating that about 19% of the TMA did not react and was distilled out with the toluene/xylene. The remainder formed MAO.

EXAMPLE 2

This experiment was the same as Example 1 except the TMA/toluene solution was 9.8 weight % TMA, and both the TMA/xylene and water dispersion were pumped at about 350–400 mL/min into the T-reactor. The TMA/xylene temperature was 22° C. and the water dispersion was 13° C. The reaction again proceeded very smoothly. The product from the T-reactor was collected in two flasks as follows.

|  | Before Strip | After Strip |
| --- | --- | --- |
| Flask 1 | | |
| Net wt (g) | 1362 | 433 |
| Percent Al | | 2.84 |
| Gas/Al ratio | | 1.79 |
| Activity | | 27 |
| Flask 2 | | |
| Net wt (g) | 1043 | 669.2 |
| Percent Al | | 1.96 |
| Gas/Al ratio | | 2.18 |
| Activity | | 23.6 |

EXAMPLE 3

This experiment was conducted in the same T-reactor set-up used in Example 1 except that a thermocouple was inserted immediately after the T-reactor. Feed streams and flow rates were:

| TMA/toluene | 9 wt % TMA |
| --- | --- |
| TMA/toluene flow rate | 400 mL/min |
| Water/xylene | 1 wt % water |
| Water/xylene flow rate | 250 mL/min |

The water/xylene emulsion was within a 12°–18° C. temperature range and the TMA/toluene feed was at 7°–11° C. The temperature following the T-reactor ranged from 13°–15° C. and the temperature in the collection flasks was 9.5°–22° C.

|  | Before Strip | After Strip |
| --- | --- | --- |
| Flask 1 | | |
| Net wt (g) | 1506 | 682.2 |
| Activity | | 29.6 |
| Flask 2 | | |
| Net wt (g) | 1276 | 788.9 |
| Activity | | 23.0 |

EXAMPLE 4

This example used the same set-up as in Example 3. The following data describes the run.

| % TMA in toluene | 9.8 |
| --- | --- |
| TMA/toluene temp. (°C.) | 4.5–7.5 |
| TMA/toluene flow rate (mL/min) | 300 |
| % H$_2$O in xylene | 1.53 |
| H$_2$O/xylene temp. (°C.) | 14–20 |
| H$_2$O/xylene flow rate (mL/min) | 300 |
| Post T-reactor temp. (°C.) | 17–21 |

Product from the T-reactor was collected in two flasks, A and B.

|  | Flask A | Flask B |
| --- | --- | --- |
| Collection flask temp (°C.) | 14–20 | 14–20 |
| Net wt. before strip (g) | 1431 | 1117 |
| Net wt. after strip | | 515.5 |
| % Al after strip | 3.72 | 3.18 |
| Gas/Al ratio | 1.65 | 1.72 |
| Activity | 19.5 | 20.1 |

EXAMPLE 5

This example used the same set-up and general procedure as in Example 3. Specific details are as follows.

|  | Flask A | Flask B |
| --- | --- | --- |
| % TMA in toluene | 9.8 | 9.8 |
| TMA/toluene temp (°C.) | 5.2–6.7 | 10.3–10.8 |
| TMA/tolune flow rate (mL/min) | 300–350 | 375 |
| % H$_2$O in xylene | 1.0 | 1.0 |
| H$_2$O/xylene temp (°C.) | 18.4–20.4 | 17.4–17.9 |
| H$_2$O/xylene flow rate (mL/min) | 300–350 | 350–375 |
| Post T-reactor temp (°C.) | 20–21.8 | 27.8–28 |
| Net wt after strip (g) | 749 | 750.9 |
| % Al after strip | 2.72 | 2.67 |
| Activity | 15.5 | 18.3 |

EXAMPLE 6

This example used the same set-up and general procedure as in Example 3. Specific details were as follows.

| % TMA in toluene | 9.8 |
| --- | --- |
| TMA/toluene temp. (°C.) | 5–10 |
| TMA/toluene flow rate (mL/min) | 275–375 |
| % H$_2$O in xylene | 1.0 |
| H$_2$O/xylene temp (°C.) | 17–20 |
| H$_2$O/xylene flow rate (mL/min) | 275–375 |

|  | Flask A | Flask B |
| --- | --- | --- |
| Net wt after strip (g) | 749 | 750.9 |
| Activity | 15.5 | 18.2 |

The above results show that the MAO made by the present process consistently exhibits co-catalyst activity which exceeds that required by industry.

I claim:
1. A process for making a hydrocarbyl aluminoxane, said process comprising:
   (A) forming a solution of about 1–30 weight percent of a hydrocarbyl aluminum compound in a dry inert hydrocarbon solvlent,
   (B) conducting an inert hydrocarbon solvent containing 0.25–5.0 weight percent of a separate water phase through a static mixer comprising a plurality of deflection elements which provide a tortuous path through said static mixer thereby dispersing said water in the hydrocarbon solvent to form a water dispersion,
   (C) conducting both (1) said hydrocarbyl aluminum compound solution and (2) said water dispersion at a velocity of about 0.5–20 ft/sec to a reaction zone whereby said hydrocarbyl aluminum compound solution and said water dispersion enter said reaction zone and co-mingle, one with the other, and react to form a hydrocarbyl aluminoxane solution further characterized in that the ratio of aluminum atoms to moles of water entering said reaction zone is in the range of 1:1 to 2:1, and (D) promptly removing said hydrocarbyl aluminumoxane solution from said reaction zone through an outlet conduit at a rate such that the total residence time in said outlet conduit is from 1 milisecond to 1 minute.

2. A process of claim 1 wherein said hydrocarbyl aluminum compound is a trialkyl aluminum.

3. A process of claim 2 wherein said solution of hydrocarbyl aluminum compound and said water dispersion are at a temperature of −20° C. to 20° C. prior to entering said reaction zone.

4. A process of claim 3 wherein said trialky aluminum compound is selected from trimethyl aluminum, triethyl aluminum and triisobutyl aluminum.

5. A process of claim 4 wherein said trialkyl aluminum is trimethyl aluminum.

6. A process of claim 1 wherein said reaction zone is defined by intersecting conduits in the configuration of a T wherein the first arm of said T is an inlet conduit for said solution of hydrocarbyl aluminum, a second arm of said T is an inlet conduit for said water dispersion and a third arm of said T is an outlet conduit leading from said reaction zone.

7. A process of claim 6 wherein said hydrocarbyl aluminum compound is a trialkyl aluminum compound.

8. A process of claim 7 wherein said aluminoxane solution removed from said reaction zone is transferred to a reaction vessel wherein any remaining trialkyl aluminum and water in said aluminoxane solution continue reacting to complete the formation of aluminoxane.

9. A process of claim 8 wherein said outlet conduit from said reaction zone is operably connected to said reaction vessel to conduct said aluminoxane solution from said reaction zone to said reaction vessel.

10. A process of claim 9 wherein said trialkyl aluminum solution and said water dispersion are cooled to a temperature in the range of −20° to 20° C. prior to entering said reaction zone.

11. A process of claim 10 wherein said trialkyl aluminum is trimethyl aluminum and said hydrocarbyl aluminoxane is methylaluminoxane.

12. A process of claim 11 wherein (1) said inlet conduit for said solution of trimethyl aluminum and (2) said inlet conduit for said water dispersion comprise the upper substantially horizontal converging arms of said T and the remaining arm of said T is an outlet conduit from said reaction zone operably connected to said reaction vessel.

13. A process of claim 12 wherein the total residence time of said aluminoxane solution in said outlet conduit and said conduit operably connected to said reaction vessel is from 1 milisecond to 1 minute.

14. A process of claim 6 wherein the T-reactor is located inside of a reaction vessel such that the outlet from said T-reactor discharges said hydrocarbyl aluminoxane solution inside said reaction vessel and said hydrocarbyl aluminoxane solution is removed from said reaction vessel at a rate that maintains a substantially constant liquid level in said finishing reaction vessel and said T-reactor is located below said liquid level.

15. A process of claim 14 wherein said hydrocarbyl aluminum compound is a trialkyl aluminum.

16. A process of claim 15 wherein said trialkyl aluminum is trimethyl aluminum.

17. A process of claim 16 wherein the solution of trimethyl aluminum in an inert hydrocarbon solvent is at a temperature of −20° to 20° C. and said water dispersion is at a temperature of 0° to 20° C. prior to entering said T-reactor.

18. A process of claim 17 wherein said T-reactor is oriented as an inverted T inside said reaction vessel.

19. A process of claim 18 wherein said inert hydrocarbon solvent is toluene.

* * * * *